US011674223B2

(12) United States Patent
Frankel et al.

(10) Patent No.: US 11,674,223 B2
(45) Date of Patent: Jun. 13, 2023

(54) REACTOR FOR COATING PARTICLES IN STATIONARY CHAMBER WITH ROTATING PADDLES AND GAS INJECTION

(71) Applicant: Applied Materials, Inc., Santa Clara, CA (US)

(72) Inventors: Jonathan Frankel, Los Gatos, CA (US); Colin C. Neikirk, Sunnyvale, CA (US); Pravin K. Narwankar, Sunnyvale, CA (US); Quoc Truong, San Ramon, CA (US); Govindraj Desai, Karnataka (IN); Sekar Krishnasamy, Bangalore (IN); Shrikant Swaminathan, Santa Clara, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 16/855,871

(22) Filed: Apr. 22, 2020

(65) Prior Publication Data
US 2020/0338521 A1    Oct. 29, 2020

Related U.S. Application Data

(60) Provisional application No. 62/838,237, filed on Apr. 24, 2019.

(51) Int. Cl.
*C23C 16/44*     (2006.01)
*C23C 16/455*    (2006.01)
(Continued)

(52) U.S. Cl.
CPC ........ *C23C 16/4417* (2013.01); *B01F 27/051* (2022.01); *B01F 27/074* (2022.01);
(Continued)

(58) Field of Classification Search
CPC .............. B01F 7/00016; B01F 7/00158; B01F 7/00191; B01F 7/0025; B01F 7/04;
(Continued)

(56) References Cited

U.S. PATENT DOCUMENTS

| 1,590,370 A | * | 6/1926 | Hallquist | ................ | D06F 17/12 |
| | | | | | 68/183 |
| 2,564,745 A | * | 8/1951 | Wintermyer | ........... | G01N 33/24 |
| | | | | | 366/165.2 |

(Continued)

FOREIGN PATENT DOCUMENTS

| CN | 105648422 | 6/2016 |
| CN | 205667839 | 11/2016 |

(Continued)

OTHER PUBLICATIONS

Didden et al., "Fluidized-bed atomic layer deposition reactor for the synthesis of core-shell nanoparticles" Review of Scientific Instruments, 2014, 85:013905-1-8.

(Continued)

*Primary Examiner* — Charles Cooley
(74) *Attorney, Agent, or Firm* — Fish & Richardson P.C.

(57) ABSTRACT

A reactor for coating particles includes a stationary vacuum chamber having a lower portion that forms a half-cylinder and an upper portion to hold a bed of particles to be coated, a vacuum port in the upper portion of the chamber, a paddle assembly, a motor to rotate a drive shaft of the paddle assembly, a chemical delivery system to deliver a first fluid, and a first gas injection assembly to receive the first fluid from the chemical delivery system and having apertures configured to inject a first reactant or precursor gas into the lower portion of the chamber and such that the first reactant or precursor gas flows substantially tangent to a curved inner surface of the half-cylinder.

18 Claims, 6 Drawing Sheets

Figure 1:
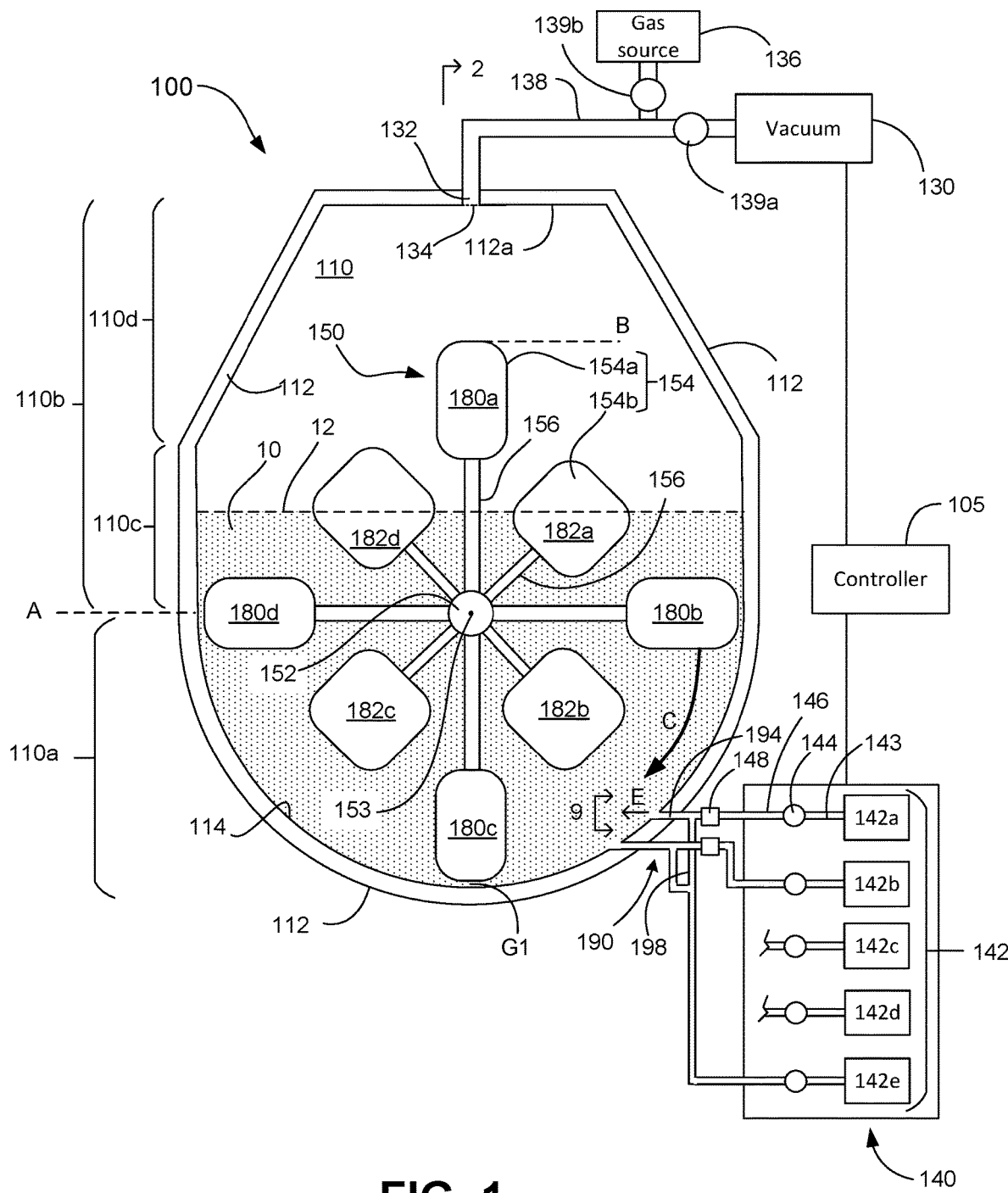

(51) Int. Cl.
*B01J 19/00* (2006.01)
*B01J 19/18* (2006.01)
*B01F 27/051* (2022.01)
*B01F 27/70* (2022.01)
*B01F 27/07* (2022.01)
*B01F 27/112* (2022.01)
*B01F 27/072* (2022.01)

(52) U.S. Cl.
CPC ........ *B01F 27/0726* (2022.01); *B01F 27/112* (2022.01); *B01F 27/70* (2022.01); *B01J 19/0066* (2013.01); *B01J 19/18* (2013.01); *C23C 16/45555* (2013.01)

(58) Field of Classification Search
CPC .... B01F 13/0211; B01F 13/06; B01F 27/051; B01F 27/0726; B01F 27/074; B01F 27/112; B01F 27/70; B01F 33/402; B01F 33/70; B01J 19/0066; B01J 19/18; C23C 16/4417; C23C 16/45555; C23C 16/442; C23C 16/45544; C23C 16/45523; C23C 16/45589; A61K 9/5089
USPC ....... 366/139, 165.1–165.5; 422/225; 118/50
See application file for complete search history.

(56) References Cited

U.S. PATENT DOCUMENTS

| | | | |
|---|---|---|---|
| 2,992,813 A * | 7/1961 | Bonomo | A21C 1/06 366/97 |
| 3,208,732 A * | 9/1965 | Ranson | A47J 43/24 426/481 |
| 3,304,063 A * | 2/1967 | Ranson | A47J 43/24 285/8 |
| 3,818,982 A | 6/1974 | Wagner | |
| 4,726,686 A * | 2/1988 | Wolf | F02M 33/02 210/512.1 |
| 6,015,606 A | 1/2000 | Abe | |
| 6,074,085 A * | 6/2000 | Scarpa | B05B 7/1431 366/178.2 |
| 6,613,383 B1 | 9/2003 | George et al. | |
| 8,162,531 B2 | 4/2012 | Crump | B01F 25/21 366/173.2 |
| 9,951,419 B2 | 4/2018 | Jiang et al. | |
| 11,174,552 B2 * | 11/2021 | Neikirk | C23C 16/45544 |
| 11,180,851 B2 * | 11/2021 | Neikirk | C23C 16/4417 |
| 11,299,806 B2 * | 4/2022 | Frankel | B01F 27/051 |
| 2003/0175186 A1 * | 9/2003 | Cohen | B01F 27/90 422/231 |
| 2004/0040503 A1 * | 3/2004 | Basceri | C23C 16/45574 118/715 |
| 2007/0213212 A1 | 9/2007 | Abe et al. | |
| 2008/0035056 A1 | 2/2008 | Okubo et al. | |
| 2008/0254219 A1 | 10/2008 | Keun et al. | |
| 2011/0116984 A1 | 5/2011 | Rehmat et al. | |
| 2011/0200822 A1 | 8/2011 | Detavernier et al. | |
| 2012/0009343 A1 | 1/2012 | Van Ommen | |
| 2013/0059073 A1 | 3/2013 | Jiang et al. | |
| 2014/0014270 A1 * | 1/2014 | Shah | B01F 23/19 366/165.2 |
| 2014/0127756 A1 | 5/2014 | Bolz et al. | |
| 2015/0125599 A1 | 5/2015 | Lindfors et al. | |
| 2016/0068758 A1 | 3/2016 | Linck et al. | |
| 2017/0062191 A1 | 3/2017 | Zafiropoulo et al. | |
| 2017/0137940 A1 | 5/2017 | Zeberoff et al. | |
| 2018/0019468 A1 * | 1/2018 | Zhu | H01M 4/0416 |
| 2018/0221294 A1 | 8/2018 | Carlsson et al. | |
| 2019/0062914 A1 | 2/2019 | King et al. | |
| 2019/0099328 A1 | 4/2019 | Zhu et al. | |
| 2019/0376181 A1 * | 12/2019 | Neikirk | C23C 16/45578 |
| 2019/0376182 A1 * | 12/2019 | Neikirk | B01J 3/02 |
| 2020/0338008 A1 * | 10/2020 | Wang | A61K 9/5031 |
| 2020/0338517 A1 * | 10/2020 | Frankel | C23C 16/4485 |
| 2020/0338521 A1 * | 10/2020 | Frankel | C23C 16/45555 |
| 2020/0340108 A1 * | 10/2020 | Frankel | B01F 27/051 |
| 2022/0032258 A1 * | 2/2022 | Desai | C23C 16/4481 |
| 2022/0064794 A1 * | 3/2022 | Neikirk | B01J 15/00 |
| 2022/0205091 A1 | 6/2022 | Frankel et al. | |

FOREIGN PATENT DOCUMENTS

| | | |
|---|---|---|
| JP | 2001-524603 | 12/2001 |
| JP | 2004-047887 | 2/2004 |
| JP | 2009-511754 | 3/2009 |
| WO | WO 2007/049873 | 5/2007 |
| WO | WO 2007/123510 | 11/2007 |
| WO | WO 2014/044907 | 3/2014 |

OTHER PUBLICATIONS

King et al., "Atomic layer deposition on particles using a fluidized bed reactor with in situ mass spectrometry," Surface & Coatings Technology, 2007, 201(22-23):9163-71.
PCT International Search Report and Written Opinion in International Appln. No. PCT/US2020/029365, dated Jul. 29, 2020, 13 pages.
TW Office Action in Taiwanese Appln. No. 109113266, dated Jan. 11, 2021, 7 pages (with English Search Report).
Office Action in Taiwanese Appln. No. 110128659, dated Jan. 14, 2022, 4 pages (with English Search Report).
Office Action in Japanese Appln. No. 2021-563228, dated Nov. 22, 2022, 5 pages (with English translation).
Extended European Search Report in European Appln No. 20795840.6, dated Dec. 21, 2022, 10 pages.

* cited by examiner

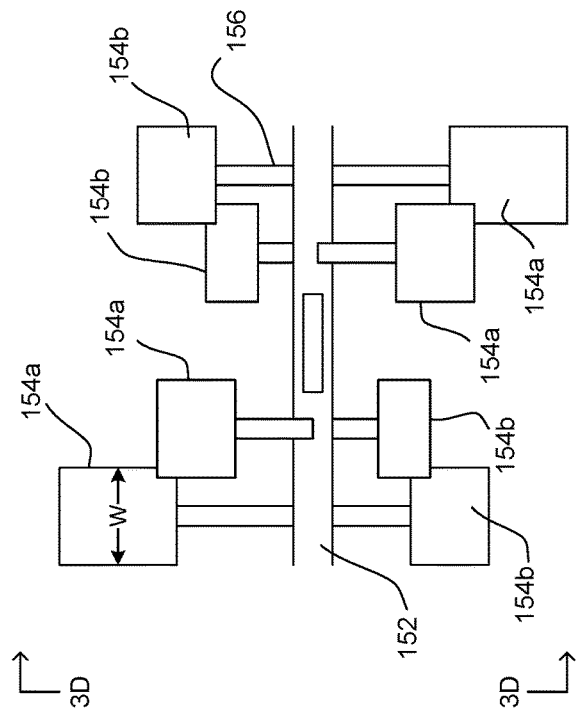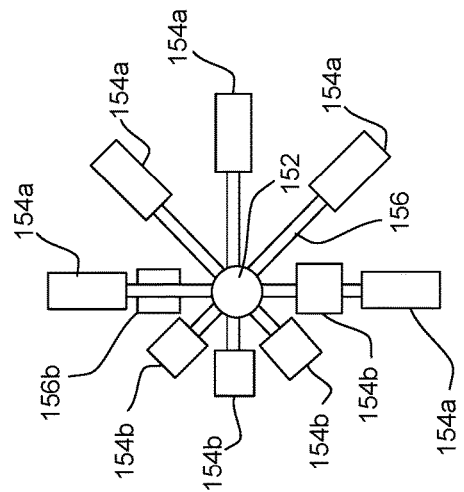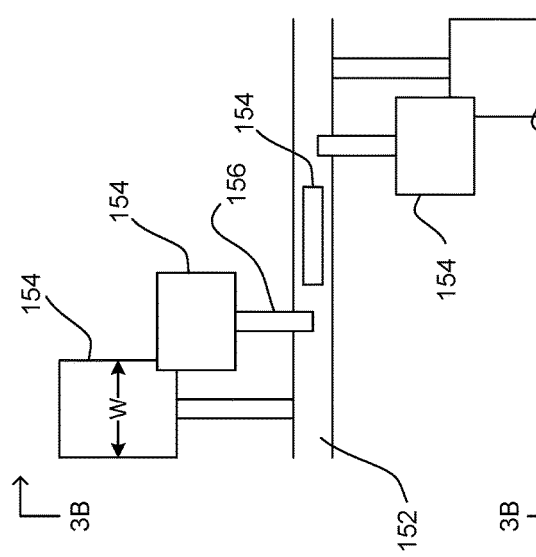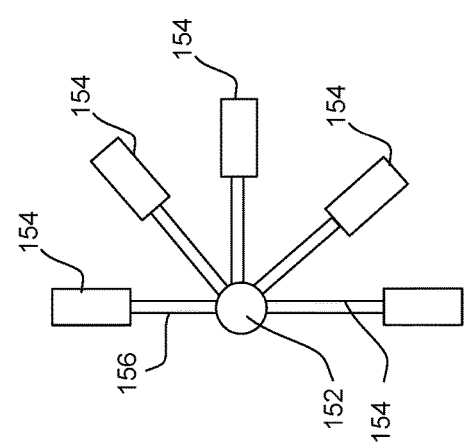
FIG. 3C
FIG. 3D
FIG. 3A
FIG. 3B

REACTOR FOR COATING PARTICLES IN STATIONARY CHAMBER WITH ROTATING PADDLES AND GAS INJECTION

CROSS-REFERENCE TO RELATED APPLICATIONS

This application claims priority to U.S. Provisional Application Ser. No. 62/838,237, filed on Apr. 24, 2019, the entire disclosure of which is incorporated by reference.

TECHNICAL FIELD

This disclosure pertains coating particles, e.g., particles that include active pharmaceutical ingredients, with thin organic and inorganic films.

BACKGROUND

It is of great interest to the pharmaceutical industry to develop improved formulations of active pharmaceutical ingredients (API). Formulation can influence the stability and bioavailability of the API as well as other characteristics. Formulation can also influence various aspects of drug product (DP) manufacture, for example, ease and safety of the manufacturing process.

Numerous techniques for encapsulating or coating API have been developed. Some existing techniques for the coating of API include spray coating, plasma polymerization, hot wire chemical vapor deposition (CVD), and rotary reactors. Spray coating is an industrially scalable technique that has been widely adopted by the pharmaceutical industry. However, coating non-uniformities (both within particle and from particle to particle) prevent the use of these techniques for improving the delivery profile or stability of active pharmaceutical ingredients (APIs). Particle agglomeration during spray coating also causes significant challenges. Meanwhile, techniques such as plasma polymerization are difficult to scale, applicable only to certain precursor chemistries, and can result in the degradation of sensitive APIs. Existing hot-wire CVD processes utilizing hot wire radical sources inside the reaction vessel are poorly scalable and are not suitable for thermally sensitive APIs. Rotary reactors include atomic layer deposition (ALD) and initiated CVD (iCVD) reactors. However, ALD reactors are suitable for inorganic coatings and not for organic polymer coatings, and existing iCVD designs do not adequately prevent API degradation and are not scalable for high volume manufacturing. Other techniques include polymer mesh coating, pan coating, aerosolized coating, and fluidized bed reactor coating.

SUMMARY

In one aspect, a reactor for coating particles includes a stationary vacuum chamber having a lower portion that forms a half-cylinder and an upper portion to hold a bed of particles to be coated, a vacuum port in the upper portion of the chamber, a paddle assembly, a motor to rotate a drive shaft of the paddle assembly, a chemical delivery system to deliver a first fluid, and a first gas injection assembly to receive the first fluid from the chemical delivery system and having apertures configured to inject a first reactant or precursor gas into the lower portion of the chamber such that the first reactant or precursor gas flows substantially tangent to a curved inner surface of the half-cylinder. The paddle assembly includes a rotatable drive shaft extending through the chamber along the axial axis of the half cylinder, and a plurality of paddles extending radially from the drive shaft such that rotation of the drive shaft by the motor orbits the plurality of paddles about the drive shaft.

In another aspect, a method of coating particles includes dispensing particles into a vacuum chamber to fill at least a lower portion of the chamber that forms a half-cylinder, evacuating the chamber through a vacuum port in an upper portion of the chamber, rotating a paddle assembly such that a plurality of paddles orbit a drive shaft, and injecting a reactant or precursor gas into the lower portion of the chamber as the paddle assembly rotates such that the first reactant or precursor gas flows substantially tangent to a curved inner surface of the half-cylinder.

Implementations may include one or more of the following features.

The first gas injection assembly may be configured to inject the reactant or precursor gas in a direction perpendicular to the axial axis. The first gas injection assembly may have a first plurality of apertures extending in a first row parallel to the axial axis, and the first gas injection assembly may be configured to inject the reactant or precursor gas through the first plurality of apertures. The first plurality of apertures may be positioned in a lower half of the lower portion of the chamber. The first plurality of apertures may be positioned in a lower quarter of the lower portion of the chamber.

The chemical delivery system may be configured to deliver a second fluid, and a second gas injection assembly may receive the second fluid from the chemical delivery system and have apertures configured to inject a second reactant or precursor gas into the lower portion of the chamber such that the second reactant or precursor gas flows substantially tangent to a curved inner surface of the half-cylinder. The second gas injection assembly may include a second plurality of apertures extending in a second row parallel to the axial axis, and the second gas injection assembly may be configured to inject the second reactant or precursor gas through the second plurality of apertures.

The first gas injection assembly may include a manifold and a plurality of channels extending from the manifold to the first plurality of nozzles. Each channel opens in a ceiling of a corresponding aperture. A restriction may be formed between the manifold and the plurality of channels.

In another aspect, a reactor for coating particles includes a stationary vacuum chamber that has a lower portion that forms a half-cylinder and an upper portion and that holds a bed of particles to be coated, a vacuum port in the upper portion of the chamber, a paddle assembly, a motor to rotate the drive shaft, a chemical delivery system to deliver a plurality of fluids including at least a first liquid, and a first gas injection assembly to receive the first liquid from the chemical delivery system. The first gas injection assembly includes a vaporizer to convert the first liquid to a first reactant or precursor gas, a manifold to receive the first reactant or precursor gas from the vaporizer, and a plurality of channels leading from the manifold to a plurality of apertures located in the lower portion of the chamber. The paddle assembly includes a rotatable drive shaft extending through the chamber along the axial axis of the half cylinder, and a plurality of paddles extending radially from the drive shaft such that rotation of the drive shaft by the motor orbits the plurality of paddles about the drive shaft.

In another aspect, a method of coating particles includes dispensing particles into a vacuum chamber to fill at least a lower portion of the chamber that forms a half-cylinder, evacuating the chamber through a vacuum port in an upper portion of the chamber, rotating a paddle assembly such that a plurality of paddles orbit a drive shaft, flowing a reactant or precursor from a chemical delivery system to a vaporizer, converting the first liquid to a first reactant or precursor gas in the vaporizer, and passing the gas from the vaporizer through a manifold and a plurality of channels to a plurality of apertures located in the lower portion of the chamber.

Implementations may include one or more of the following features.

The vaporizer may be positioned immediately adjacent the manifold. The vaporizer, manifold and passages may be formed in a unitary body.

A passage from the chemical delivery system may be configured to deliver an inert gas from the chemical delivery system to the manifold. The passage may be fluidically connected directly to the manifold. The passage may be fluidically connected directly to an inlet that carries the first liquid. The vaporizer may have a cavity, a heater to heat walls of the cavity, and a nozzle to aerosolize the first liquid as the first liquid passes into cavity. The passage may be fluidically connected directly to the cavity.

Implementations may include, but are not limited to, one or more of the following possible advantages. Particles, e.g., API particles, can be coated with in a high volume manufacturing process, thereby providing lower cost of manufacturing and reduced drug product prices. Particles can be coated with a thin layers, thus providing a drug product with an advantageous volume fraction of API. In addition, the process can result in layer(s) encapsulating the API that are uniform within a particle and from particle-to-particle, providing more consistent properties to the drug formulations.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting.

Other features and advantages of the invention will be apparent from the following detailed description and figures, and from the claims.

BRIEF DESCRIPTION OF THE DRAWINGS

FIG. 1 is a schematic front view of a reactor for ALD and/or CVD coating of particles, e.g., drugs, that includes a stationary drum.

FIG. 2 is a schematic side view of the reactor of FIG. 1. FIG. 2 can be taken along line 2-2 in FIG. 1.

FIG. 3A is a schematic side view of a paddle assembly.

FIG. 3B is a front side view of the paddle assembly of FIG. 3A. FIG. 3B can be taken along line 3B-3B in FIG. 3A.

FIG. 3C is a schematic side view of another implementation of a paddle assembly.

FIG. 3D is a front side view of the paddle assembly of FIG. 3C. FIG. 3D can be taken along line 3D-3D in FIG. 3C.

FIG. 4 is a schematic perspective view of a paddle.

FIG. 5 is a schematic side view of a group of paddles from a paddle assembly.

FIG. 6A is a schematic side view of another implementation of a group of paddles from a paddle assembly.

FIG. 6B is a schematic side view of yet another implementation of a group of paddles from a paddle assembly.

FIG. 7 is a schematic side view of a paddle from the group of paddles in FIG. 5 or 6. FIG. 7 can be taken along line 7-7 in FIG. 5.

FIG. 8 is a schematic side view of gas injection ports. FIG. 8 can be taken along line 8-8 in FIG. 1.

FIG. 9 is a schematic top view the gas injection ports of FIG. 8.

FIG. 10 is a schematic perspective view, partially cross-sectional, showing a gas injection assembly.

Like reference numbers and designations in the various drawings indicate like elements.

DETAILED DESCRIPTION

There are various methods for encapsulating API particles. In many cases, these methods result in a coating that is relatively thick. While such coatings can impart desirable properties, the high ratio of coating to API can make it difficult to create a drug product in which the volume fraction of API is as high as desired. In addition, the coating encapsulating the API can be non-uniform, making it difficult to provide formulations with consistent properties. Furthermore, coating techniques that can provide satisfactory consistency have not be scalable for industrial manufacturing.

An approach that may address these issues is to use a stationary "drum" in which particles are agitated by rotating paddles, and process gas is injected into the drum through the drum sidewall. This can force the process gas to percolate through the particle bed, which can improve uniformity of coating across the particles Another issue is that particles tend to agglomerate in the reaction chamber. As a result, process gas might not coat the regions where the particles contact, leading to non-uniform coating. Although stirring the particle bed with paddles can prevent some agglomeration, the particles can still tend to form micro-aggregates, e.g., clumps of up to 10× the primary particle size. In some techniques, the powder is removed from the reactor to perform de-aggregation. However, removal of the powder can significantly impact throughput, and can provide an opportunity for contamination or spillage.

An approach that may address this issue is to flow process and/or purge gas through the particle bed at a velocity sufficient to de-agglomerate the particles.

The particles treated using the apparatus and methods discussed below can have an average particle size (D50) in the 1-30 μm range, e.g., 1-10 μm range, although nano-scale particles are also possible. The particles can include both API and an excipient, or the particles can consist of API.

Drug

The term "drug," in its broadest sense includes all small molecule (e.g., non-biologic) APIs. The drug could be selected from the group consisting of an analgesic, an anesthetic, an anti-inflammatory agent, an anthelmintic, an anti-arrhythmic agent, an antiasthma agent, an antibiotic, an anticancer agent, an anticoagulant, an antidepressant, an antidiabetic agent, an antiepileptic, an antihistamine, an antitussive, an antihypertensive agent, an antimuscarinic agent, an antimycobacterial agent, an antineoplastic agent, an antioxidant agent, an antipyretic, an immunosuppressant, an immunostimulant, an antithyroid agent, an antiviral agent, an anxiolytic sedative, a hypnotic, a neuroleptic, an astringent, a bacteriostatic agent, a beta-adrenoceptor blocking agent, a blood product, a blood substitute, a bronchodilator, a buffering agent, a cardiac inotropic agent, a chemotherapeutic, a contrast media, a corticosteroid, a cough suppressant, an expectorant, a mucolytic, a diuretic, a dopaminergic, an antiparkinsonian agent, a free radical scavenging agent, a growth factor, a haemostatic, an immunological agent, a lipid regulating agent, a muscle relaxant, a parasympathomimetic, a parathyroid calcitonin, a biphosphonate, a prostaglandin, a radio-pharmaceutical, a hormone, a sex hormone, an anti-allergic agent, an appetite stimulant, an anoretic, a steroid, a sympathomimetic, a thyroid agent, a vaccine, a vasodilator and a xanthine.

Exemplary types of small molecule drugs include, but are not limited to, acetaminophen, clarithromycin, azithromycin, ibuprofen, fluticasone propionate, salmeterol, pazopanib HCl, palbociclib, and amoxicillin potassium clavulanate.

Pharmaceutically Acceptable Excipients, Diluents, and Carriers

Pharmaceutically Acceptable Excipients Include, but are not Limited to:

(1) surfactants and polymers including: polyethylene glycol (PEG), polyvinylpyrrolidone (PVP), sodium lauryl sulfate, polyvinylalcohol, crospovidone, polyvinylpyrrolidone-polyvinylacrylate copolymer, cellulose derivatives, hydroxypropylmethyl cellulose, hydroxypropyl cellulose, carboxymethylethyl cellulose, hydroxypropyllmethyl cellulose phthalate, polyacrylates and polymethacrylates, urea, sugars, polyols, carbomer and their polymers, emulsifiers, sugar gum, starch, organic acids and their salts, vinyl pyrrolidone and vinyl acetate;

(2) binding agents such as cellulose, cross-linked polyvinylpyrrolidone, microcrystalline cellulose;

(3) filling agents such as lactose monohydrate, lactose anhydrous, microcrystalline cellulose and various starches;

(4) lubricating agents such as agents that act on the flowability of a powder to be compressed, including colloidal silicon dioxide, talc, stearic acid, magnesium stearate, calcium stearate, silica gel;

(5) sweeteners such as any natural or artificial sweetener including sucrose, xylitol, sodium saccharin, cyclamate, aspartame, and acesulfame K;

(6) flavoring agents;

(7) preservatives such as potassium sorbate, methylparaben, propylparaben, benzoic acid and its salts, other esters of parahydroxybenzoic acid such as butylparaben, alcohols such as ethyl or benzyl alcohol, phenolic chemicals such as phenol, or quarternary compounds such as benzalkonium chloride;

(8) buffers;

(9) Diluents such as pharmaceutically acceptable inert fillers, such as microcrystalline cellulose, lactose, dibasic calcium phosphate, saccharides, and/or mixtures of any of the foregoing;

(10) wetting agents such as corn starch, potato starch, maize starch, and modified starches, and mixtures thereof;

(11) disintegrants; such as croscarmellose sodium, crospovidone, sodium starch glycolate; and

(12) effervescent agents such as effervescent couples such as an organic acid (e.g., citric, tartaric, malic, fumaric, adipic, succinic, and alginic acids and anhydrides and acid salts), or a carbonate (e.g., sodium carbonate, potassium carbonate, magnesium carbonate, sodium glycine carbonate, L-lysine carbonate, and arginine carbonate) or bicarbonate (e.g. sodium bicarbonate or potassium bicarbonate)

Metal Oxide Material

The term "metal oxide material," in its broadest sense includes all materials formed from the reaction of elements considered metals with oxygen-based oxidants. Exemplary metal oxide materials include, but are not limited to, aluminum oxide, titanium dioxide, iron oxide, gallium oxide, magnesium oxide, zinc oxide, niobium oxide, hafnium oxide, tantalum oxide, lanthanum oxide, and zirconium dioxide. Exemplary oxidants include, but are not limited to, water, ozone, and inorganic peroxide. The term "oxide material" includes metal oxide materials as well as oxides of other materials, e.g., silicon dioxide.

Atomic Layer Deposition (ALD)

Atomic layer deposition is a thin film deposition technique in which the sequential addition of self-limiting monolayers of an element or compound allows deposition of a film with thickness and uniformity controlled to the level of an atomic or molecular monolayer. Self-limited means that only a single atomic layer is formed at a time, and a subsequent process step is required to regenerate the surface and allow further deposition.

Molecular Layer Deposition (MLD)

Molecular layer deposition is analogous to atomic layer deposition but using organic precursors and forming organic thin films. During a typical MLD process two homo-bifunctional precursors are used. A first precursor is introduced into a chamber. The molecules of the first precursor react with reactive groups on the substrate surface via the corresponding linking chemistry to add a molecular layer of the first precursor on the substrate surface with new reactive sites. After purging, a second precursor is introduced and the molecules of the second precursor react with the new reactive sites provided by the first precursor generating a molecular layer of the first precursor linked to the second precursor. This is followed by another purge cycle.

Reactor System

Figure 2:
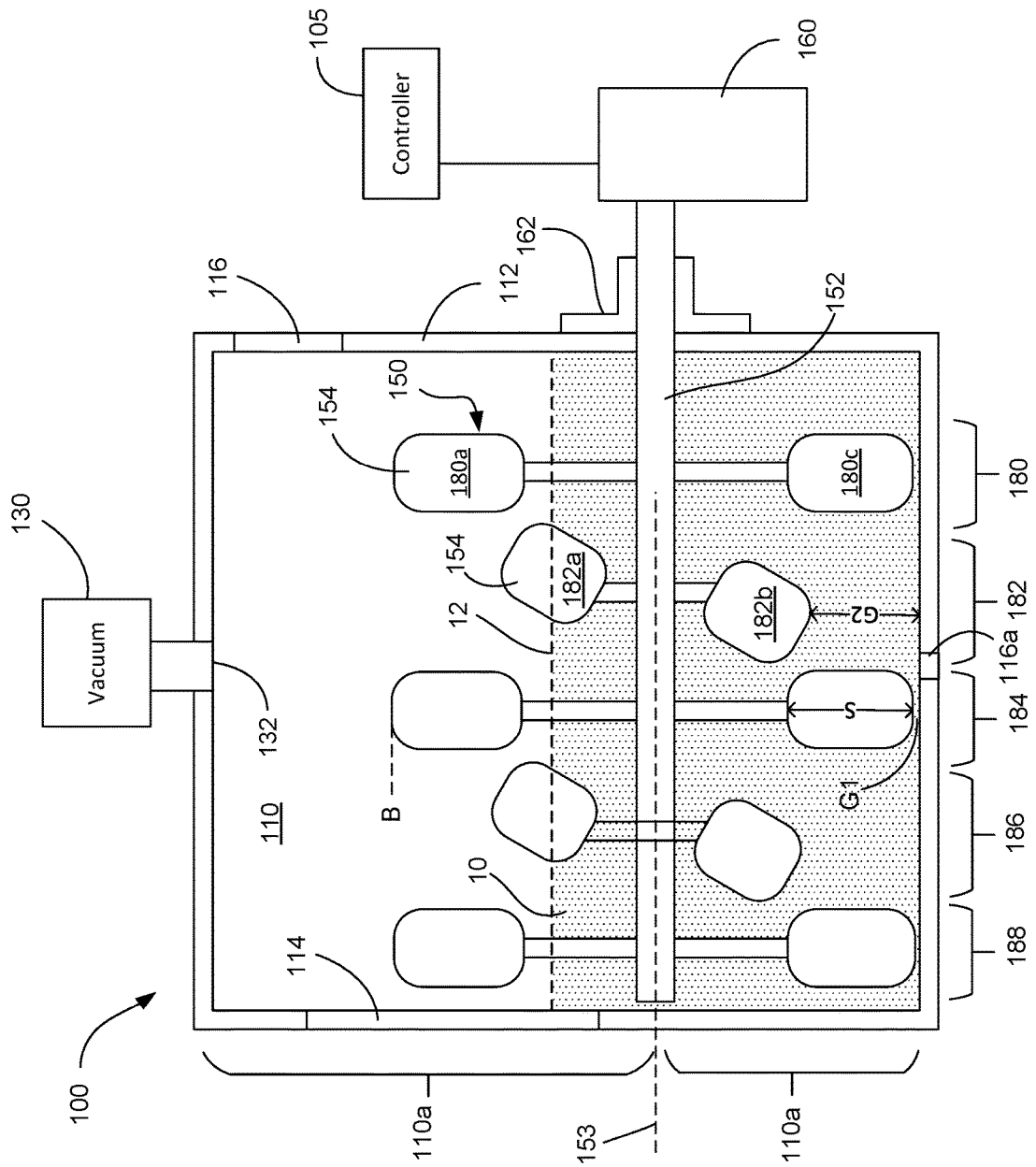

FIGS. 1-2 illustrate a reactor system 100 for coating particles with a thin-film coating. The reactor system 100 can perform the coating using ALD and/or MLD coating conditions. The reactor system 100 permits a deposition process (ALD or MLD), to be performed at higher (above 50° C., e.g., 50-100° C.) or lower processing temperature, e.g., below 50° C., e.g., at or below 35° C. For example, the reactor system 100 can form thin-film oxides on the particles primarily by ALD at temperatures of 22-35° C., e.g., 25-35° C., 25-30° C., or 30-35° C. In general, the particles can remain or be maintained at such temperatures. This can be achieved by having the reactant gases and/or the interior surfaces of the reactor chamber remain or be maintained at such temperatures.

The reactor system 100 includes a stationary vacuum chamber 110 that encloses a paddle assembly 150.

The vacuum chamber 110 is enclosed by chamber walls 112. A lower portion 110a of the chamber 110 forms a half-cylinder with a semicircular cross-section (as viewed along the central axis of the half-cylinder). The cross-section (again, as viewed along the central axis of the half-cylinder) of the upper portion 110b can be uniform along the length of the chamber 110 (the length is along the central axis of the half-cylinder). This can help ensure uniform gas flow along the length of the chamber. If gas flow is sufficiently uniform, the cross section can be non-uniform, e.g., narrowing toward the top when viewed horizontal but perpendicular to the central axis of the half-cylinder) to reduce the volume of the chamber 110.

The cross-section of the upper portion 110b can otherwise be selected to conserve space in the fabrication facility while still enclosing the paddle assembly 150. For example, the upper portion 110b of the chamber 110 can be a rectangular solid (see FIG. 6A), a half-cylinder with a semicircular cross-section, or other appropriate shape that does not block rotation of the paddle assembly 150. In some implementations, the upper portion 110b of the chamber has a lower section 110c that is adjacent the lower portion 110a and that has vertical side walls, e.g., a rectangular solid volume. An upper section 110d that extends between the lower section 110c and a ceiling 112a of the chamber 110 can have a cross-section (again, as viewed along the central axis of the half-cylinder) that is triangular or trapezoidal.

Figure 6B:
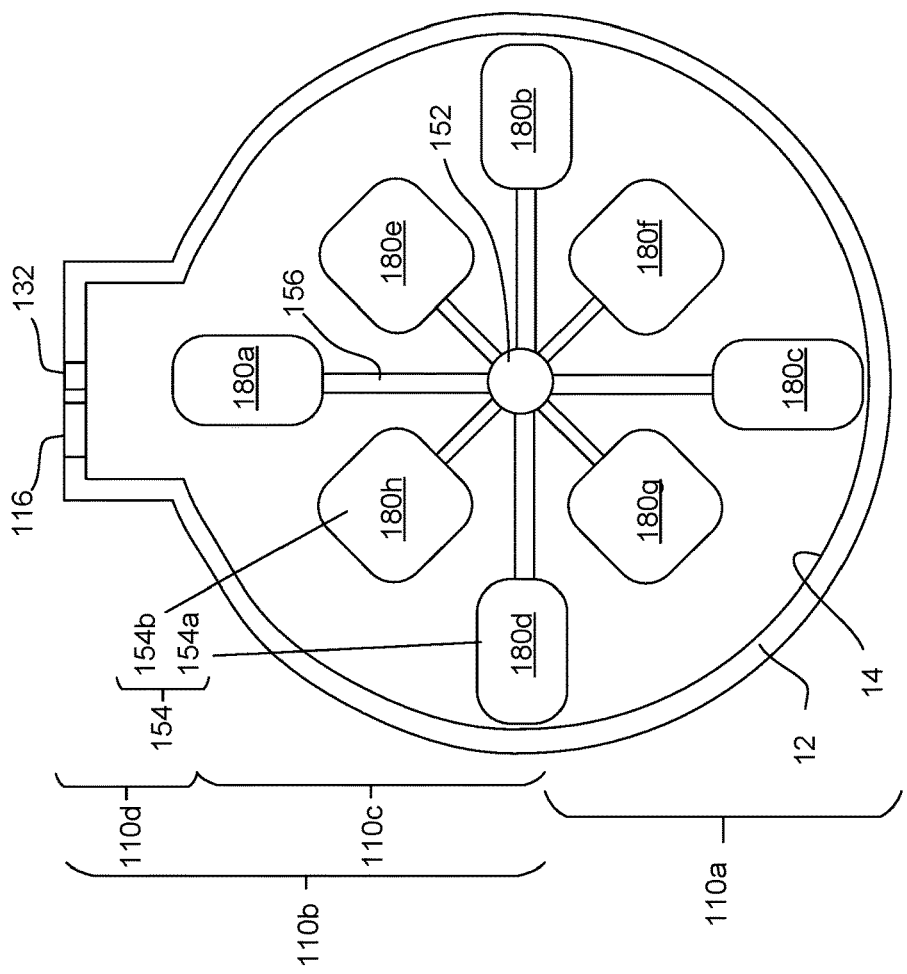
Figure 6A:
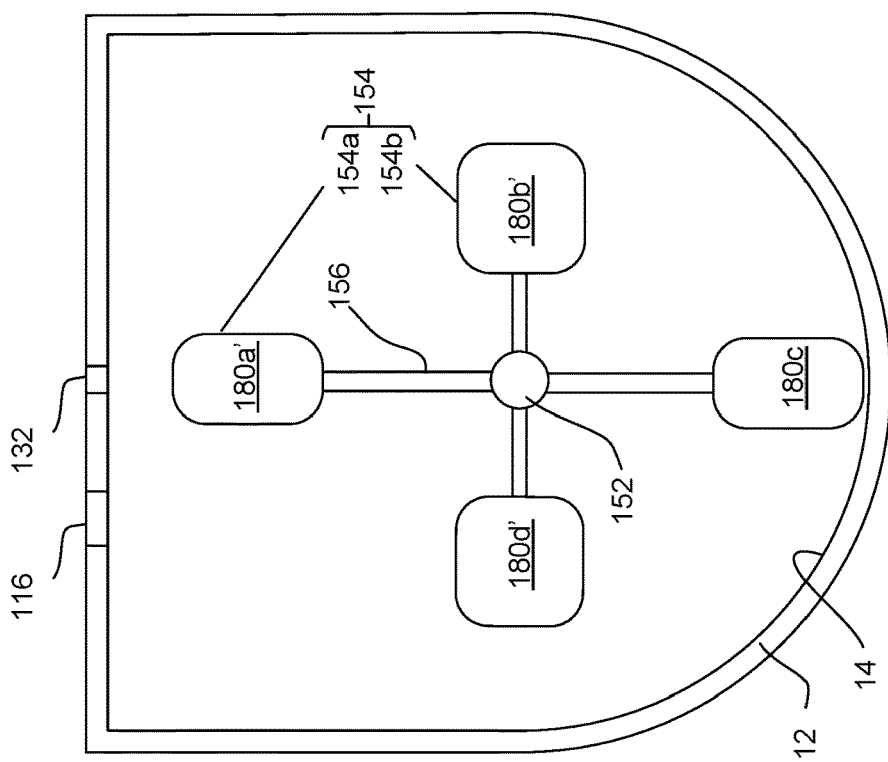

In some implementations, e.g., as shown in FIG. 6B (but which could be combined with other paddle assemblies), the curved portion of the chamber wall along the lower section 110c of the upper chamber 110b. An upper section 110d that extends between the lower section 110c and a ceiling 112a of the chamber 110 can provide a volume for a vacuum port 132 and/or a powder delivery port 116. This configuration can avoid powder build up, e.g., caused by the paddle assembly throwing the powder, along a portion of the side wall 12 that is out of reach of the paddles 154.

The chamber walls 110 can be a material, e.g., stainless steel, that is inert to the deposition process, and/or the interior surfaces of the chamber walls 110 can be coated with a material that is inert to the deposition process. In some implementations, a viewing port 114 of transparent material, e.g., quartz, can be formed through the chamber wall 112 to permit an operator to view an interior of the chamber 110.

In operation, the chamber 110 is partially filled by particles, e.g., API-containing particles, that provide a particle bed 10. For superior throughput, the particle bed 10 fills at least the lower portion 110a of the chamber, e.g., the top surface 12 of the particle bed 10 is at or above the lower portion 110a (indicated at A). On the other hand, the top surface 12 of the particle bed 10 should be below the top (indicated at B) of the paddle assembly 150 to avoid poor mixing of the particle bed. The chamber walls 112 can include one or more sealable ports 116 to permit the particles to be placed into and removed from the chamber 110.

The chamber 110 is coupled to a vacuum source 130. The port 132 through the chamber wall 112 to connect the vacuum source 130 to the chamber can be located in the upper portion 110b of the chamber 110. In particular, the port 132 can be located above the expected position of the top surface 12 of the particle bed, e.g., above the top (indicated at B) of the paddle assembly 150, e.g., in the chamber ceiling.

The vacuum source 130 can be an industrial vacuum pump sufficient to establish pressures less than 1 Torr, e.g., 1 to 100 mTorr, e.g., 50 mTorr. The vacuum source 130 permits the chamber 110 to be maintained at a desired pressure, and permits removal of reaction byproducts and unreacted process gases.

The port 132 can be covered by a filter 134 to prevent particles thrown into the gas stream by the paddle assembly from escaping the reactor chamber 110. In addition, the system can include a filter cleaner to clear particles off the filter 134. As one example, the filter cleaner can be a mechanical knocker to strike the filter; this make shake particles off the filter. As another example, a gas source 136 (which could be provided by gas source 142e) can periodically provide a pulse of inert gas, e.g., nitrogen, into the gas line 138 between the port 132 and the vacuum source 130. The pulse of gas travels through the filter 134 back toward the chamber 110 and can blow the particles off of the filter 134. Isolation valves 139a, 139b can be used to ensure that only one of the gas source 136 or vacuum source 130 is fluidically coupled at a time to the line 138.

The chamber 110 is also coupled to a chemical delivery system 140. The chemical delivery system 140 includes multiple fluid sources 142 coupled by respective delivery tubes 143, controllable valves 144, and a fluid supply line 146. The chemical delivery system 140 delivers fluid to one or more gas injection assemblies 190 that inject the fluid in a vapor form into the chamber 110. The chemical delivery system 140 can include a combination of restrictors, gas flow controllers, pressure transducers, and ultrasonic flow meters to provide controllable flow rate of the various gasses into the chamber 110. The chemical delivery system 140 can also include one or more temperature control components, e.g., a heat exchanger, resistive heater, etc., to heat or cool the various gasses before they flow into the chamber 110.

The chemical delivery system 140 can include five fluid sources 142a, 142b, 142c, 142d, 142e. Two of the fluid sources, e.g., fluid sources 142a, 142b, can provide the two chemically different precursors or reactants for the deposition process for forming an oxide layer on the particles. For example, the first fluid source 142a can provide trimethylaluminum (TMA) or titanium tetrachloride (TiCl4), whereas the fluid gas source 142b can provide water. Another two of the fluid sources, e.g., fluid sources 142c, 142d, can provide the two chemically different precursors or reactants for the deposition process for forming a polymer material on the oxide layer. For example, the third fluid source 142c can provide adipoyl chloride, and the fourth gas source 142d can provide ethylene diamine. One of the fluid sources, e.g., the fifth fluid source 142e, can provide an inert gas, e.g., argon or $N_2$, for purging between cycles or half-cycles in the deposition process.

Although FIG. 1 illustrates five fluid sources, the use of fewer gas sources could still be compatible with deposition of an oxide or polymer layer, and use of more gas sources could enable formation of an even wider variety of laminate structures.

For one or more of the fluid sources, the chemical delivery system 140 delivers the precursor or reactant in liquid form to the gas injection assembly 190. The gas injection assembly 190 includes a vaporizer 148 to convert the liquid to vapor immediately before the precursor or reactant enters an injection manifold 194. This reduces upstream pressure loss to enable more pressure loss to occur across the particle bed 10. The more pressure loss that occurs across the particle bed 10, the lower the injection apertures can be place, and the more likely that all of the precursor will be reacted as it traverses the particle bed for a given flow rate. The vaporizer 148 can be immediately adjacent the reactor side wall, e.g., secured to or housed within the reactor wall side 112.

As shown in FIG. 1, there can be a manifold 194 for each precursor or reactant fluid, and each manifold 194 can be fluidically connected separately to the chamber 110. Thus, the precursors or reactants cannot mix until actually within the chamber 110. Alternatively, the gas lines from the fluid sources 142 could be joined as a combined fluid supply line, e.g., by a valve. The gas injection assembly 190 will be discussed further below.

As noted above, a paddle assembly 150 is positioned in the chamber 110 to agitate the particles in the particle bed. The paddle assembly 150 includes a rotatable drive shaft 152 and a plurality of paddles 154. The paddles 154 are connected to the drive shaft 152 by struts 156 that extend at outward from the drive shaft 152, such that rotation of the drive shaft 152 about an axis of rotation 153 carries the paddles 154 in a circular path (see arrow C) around the axis of rotation 153. The struts 156 can extend perpendicular to the drive shaft 152. The drive shaft 152 and axis of rotation 153 can extend along the boundary between the upper portion 110b and the lower portion 110a of the chamber 110.

The drive shaft 152 is driven by a motor 160 located outside the chamber 110. For example, the drive shaft 152 can extend through the chamber wall 112 with one end coupled to the motor 160. A bearing vacuum seal 162 can be used to seal the chamber 110 from the external environment.

The other end of the drive shaft can be supported by a bearing inside the chamber 110, e.g., the end of the drive shaft 152 can fit into a recess in the inner surface of the chamber wall 112. Alternatively, the drive shaft 152 can simply be held in a cantilevered configuration with the end of the drive shaft unsupported. This can be advantageous for disassembly and cleaning. The motor 160 can rotate the drive shaft 152 and paddle assembly 150 at speeds of 0.1 to 60 rpm.

At least some of the paddles 154 are held by the struts 156 in a position such that, as the drive shaft 152 rotations, an outer edge of a paddle 154 almost contacts the interior surface 114 of the chamber wall 112. However, the outer edge of the paddle 154 remains separated from the interior surface by a small gap G1, e.g., 1 to 4 mm. The gap G1 can be as small as possible within manufacturing tolerances such that the paddle 154 does not scrape the outer wall 112.

The axis of rotation 153 of the drive shaft 152 can be parallel, e.g., collinear, with the center axis of the cylinder that defines the lower portion 110*a*. In this case, rotation of the drive shaft 152 can cause the outer edge of a paddle 154 to sweep across the half-cylinder inner surface, e.g., across the entirety of the half-cylinder inner surface, of the lower portion 110*a*.

The paddles 154 can be spaced along the drive shaft 152 so as to ensure that the paddles that almost contact the interior surface 114 provide coverage along substantially the entire length of the reactor chamber 110. In particular, the paddles 154 be spaced and have a width W (along the axis of rotation) such that there are no gaps in the volume that is swept by the paddle assembly 150*s*. In particular, the width W can be greater than the pitch of the paddles along the drive shaft 152. The paddles at the different axial positions along the length of the drive shaft can be angularly offset. For example, as shown in FIGS. 3A and 3B, the paddles 154 can be arranged in a spiral pattern around the drive shaft 152. However, many other configurations are possible for the angular offsets, e.g., alternating sides of the drive shaft.

In some implementations, some of paddles 154 are positioned radially closer to the drive shaft 152 than other paddles 154. The paddles 154*b* that are closer to the drive shaft can be termed "inner paddles," and the paddles 154*a* that are farther from the drive shaft can be termed "outer paddles." The inner and outer paddles 154*a*, 154*b* can either not be overlapping radially, or can be partially overlapping radially. For example, the inner and outer paddles can overlap by at most 20% of the radial span S of the outer paddles (e.g., G≥0.8*S).

The outer paddles 154*a* can be spaced and have a width (along the axis of rotation) such that there are no gaps in the volume being swept by the outer paddles 154*a*. In particular, the widths of the outer paddles 154*a* can be greater than the pitch of the outer paddles 154*a* along the drive shaft 152. Adjacent outer paddles 154*a* along the length of the drive shaft can be angularly offset. Similarly, the inner paddles 154*b* can also be spaced and have a width (along the axis of rotation) such that there are no gaps in the volume being swept by the inner paddles 154*b*. In particular, the widths of the inner paddles 154*b* can be greater than the pitch of the inner paddles 154*b* along the drive shaft 152. Adjacent inner paddles 154*b* along the length of the drive shaft can be angularly offset. For example, as shown in FIGS. 3C and 3D, the inner paddles 154*b* can be arranged in a first spiral around the drive shaft 152, and the outer paddles 154*a* can be arranged in a second spiral pattern around the drive shaft 152. The spirals of the inner and outer paddles 154*a*, 154*b* are shown as 180° out of phase, but this is not required.

Moreover, many other configurations are possible for the angular offsets between adjacent paddles, e.g., the paddles could be placed on alternating sides of the drive shaft.

Figure 4:
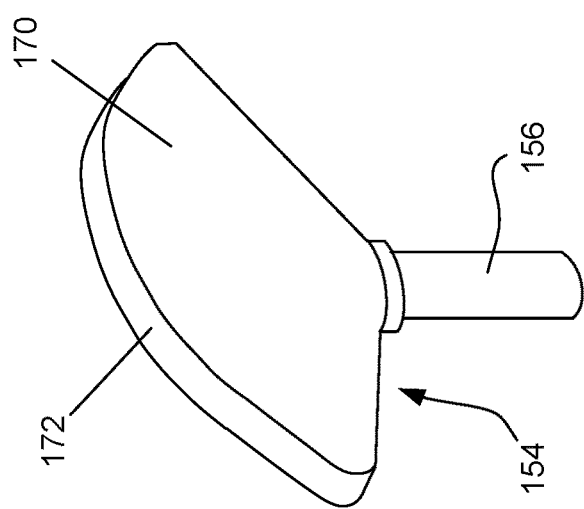

Referring to FIG. 4, each paddle 154 can be a generally planar body with a primary surface 170 to push the particles in the particle bed, and a thinner edge 172 that will contact the inner surface of the lower portion 110*a* of the chamber 110. As shown in FIG. 4, a paddle 154 can be flared with a fan-shape. Or, as shown in FIGS. 1 and 2, a paddle can be generally rectangular, e.g., rectangular with rounded edges. The surface 170 of the paddle 154 can be flat, or the surface 170 could be concave, e.g., spoon-shaped. In addition, in some implementations the paddle 154 is plough-shaped, e.g., convex or sharply convex relative to the direction of motion of the paddle.

Returning to FIG. 1, in some implementations, paddles are clustered in groups positioned in a common plane normal to the axis of rotation 153. The paddles in a group can be spaced at substantially equal angular intervals around the drive shaft 152. A group can include four paddles, although two, three or five or more paddles can be used.

Figure 5:
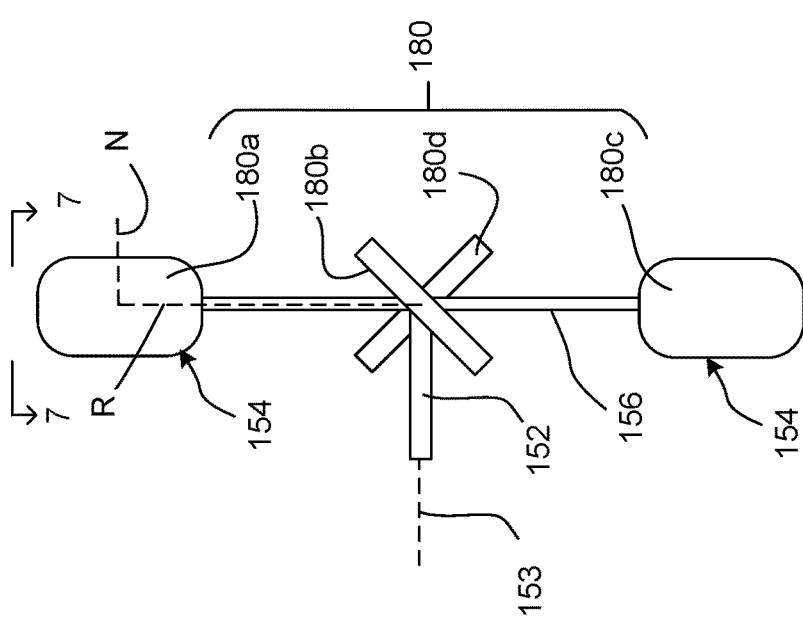

For example, referring to FIGS. 1 and 5, the paddle assembly 150 includes a group 180 of four paddles 180*a*, 180*b*, 180*c*, 180*d* spaced at 90 degree angles apart and equidistant from the drive shaft 152 and axis of rotation 153. The paddles 180*a*-180*d* can be positioned to almost contact the half-cylinder inner surface of the lower portion 110*a* of the chamber 110.

As shown in FIGS. 1 and 2, the paddle assembly 150 can include multiple groups of paddles that are positioned at different locations along the drive shaft 132. For example, the paddles assembly can include groups 180, 182, 184, 186, 188. Where there are three or more groups, the groups of paddles can be spaced at substantially equal intervals along the drive shaft 152. Each group can have the same number of paddles, e.g., four paddles. The paddles in adjacent groups can be offset angularly about the axis of rotation, e.g., by half the angle between paddles within a group. For example, if the groups have four paddles spaced 90° apart about the axis of rotation, then paddles of adjacent groups can be offset by 45°.

In some implementations, e.g., as shown in FIG. 1, the paddles in a group can be located substantially equal distances from the axis of rotation 153, e.g., the struts 156 can have the same length.

However, in some implementations, some of the paddles in a group are positioned radially closer to the drive shaft 152 than other paddles in the group. For example, the paddle assembly 150 shown in FIG. 6A includes a group of four paddles 180*a*', 180*b*', 180*c*', 180*d*' spaced at 90 degree angles apart. Two of the paddles, e.g., two opposite paddles 180*a*' and 180*c*', are located a first distance from the drive shaft 152. These two paddles can be positioned to nearly contact the half-cylindrical inner surface 112 of the lower portion 110*a*. Another two of the paddles, e.g., two opposite paddles 180*b*' and 180*d*', are located a shorter second distance from the drive shaft 152.

As another example, the paddle assembly shown in FIG. 6B includes a group of eight paddles 180*a*-180*h* spaced at 45 degree angles apart. Four outer paddles 154*a*, e.g., paddles 180*a*-180*d*, are located a first distance from the drive shaft 152. These four outer paddles 154*a* can be positioned to nearly contact the half-cylindrical inner surface 112 of the lower portion 110*a*. Four inner paddles 154*b*, e.g., paddles 180*e*-180*h*, are located a shorter second distance from the drive shaft 152. The outer paddles 154a and inner paddles 154b are placed in an alternating arrangement around the drive shaft 152.

In some implementations, some of the groups of paddles have paddles that are positioned radially closer to the drive shaft 152 than the paddles of other groups. For example, the paddle assembly 150 includes a group 182 of four inner paddles 182a, 182b, 182c, 182d spaced at 90 degree angles apart and equidistant from the drive shaft 152 and axis of rotation 153. The outer edges of the paddles 182a-182d are spaced apart from the half-cylinder inner surface of the lower portion 110a of the chamber 110 by a gap G. The inner paddles 182a-182d are radially inward compared to the outer paddles 180a-180d.

Returning to FIGS. 1, 5 and 7, each paddle 154 can be positioned and oriented such that an axis N normal to the planar face 170 of the paddle 154 is perpendicular to the radius R passing from the axis of rotation 153 to the paddle 154. However, in some implementations, one or more paddles 154 can be angled such that orbiting of the paddle 154 about the axis of rotation 153 tends to force the particles radially toward or away from axis of rotation 153.

Figure 7:
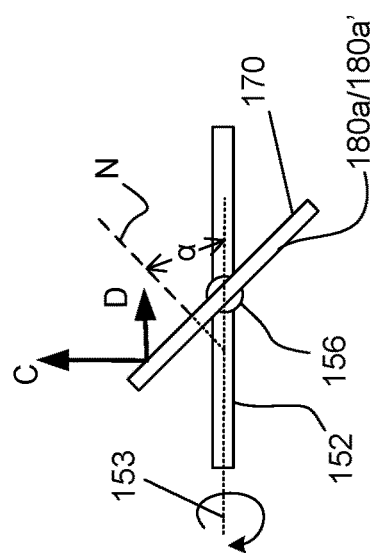

In addition, each paddle 154 can be at an oblique angle relative to the plane normal to the axis of rotation 153. In particular, each paddle 154 can be angled such that orbiting of the paddle 154 about the axis of rotation 153 tends to force the particles in a direction parallel to the axis of rotation 153. For example, as shown in FIGS. 5 and 7, a paddle 180a is oriented such that an axis N normal to the planar face 170 of the paddle 154 is at an oblique angle $\alpha$ relative to the axis of rotation 153 when viewed along the radius (e.g., parallel to the strut 156) between the paddle 180a and the axis of rotation 153. In this configuration, when the paddle orbits about the axis of rotation 153, it will have an instantaneous vector of motion C. The oblique angle $\alpha$ of the paddle 180a will drive the powder in a direction D perpendicular to the C. The oblique angle $\alpha$ can be between 15-75°, e.g., be between 30-60°, e.g., be about 45°.

The inner paddles in a group can be oriented with a common oblique angle $\alpha$, and the outer paddles in a group can be oriented with a common oblique angle $\alpha'$. In some implementations, all the inner paddles along the drive shaft 152 are oriented with a common oblique angle $\alpha$, and all the outer paddles along the drive shaft 152 are oriented with a common oblique angle $\alpha'$.

The angles $\alpha$ and $\alpha'$ are not equal. In particular, the angles $\alpha$ and $\alpha'$ can have opposite sign. In some implementations, the angle $\alpha'$ is of equal magnitude but opposite sign as the angle $\alpha$, e.g., the oblique angle is +a for the inner paddles and $-\alpha$ for the outer paddles.

In some implementations, the outer paddles 154 are angled such that orbiting of the paddles tends to force the particles in a first direction parallel to the axis of rotation 153, whereas the inner paddles 154 are angled such that orbiting of the inner paddles 154 tends to force the particles in the anti-parallel direction, i.e., a second direction opposite the first direction. For example, referring to FIGS. 6 and 7, the outer paddles 180a' and 180c' in a group 180 can force the particles in the direction D, whereas the inner paddles 180b' and 180d' in the group can force the particles in a direction opposite to D.

Referring to FIG. 2, in some implementations, a port 116a is located somewhere along, e.g., near the center of, the length of the chamber 110. The port 116a can be used to deliver and/or withdraw the particles from the reactor 100. In such an implementation, the outer paddles can be oriented to push the particles toward the port 116a, and the inner paddles can be oriented to push the particles away from the port 116a.

For example, the outer paddles of groups 180 and 182 can push the particles leftward toward the port 116a, and the inner paddles of groups 180 and 182 can push the particles rightward away from the port 116. Conversely, the outer paddles of groups 184, 186 and 188 can push the particles rightward toward the port 116a, and the inner paddles of groups 184, 186 and 188 can push the particles leftward away from the port 116a. Paddles oriented to push the particles a first direction, e.g., leftward, can be oriented with the oblique angle+a, whereas paddles oriented to push the particles in an opposite second direction, e.g., rightward, can be oriented with the oblique angle $-\alpha$.

If the paddles in each group have the same radial distance from the drive shaft, the paddles in different groups, e.g., adjacent groups, can have different oblique angles. For example, to the paddles 180a-180d in a first group 180 can force the particles in the direction D, whereas paddles 182a-182d in a second group 180 can force the particles in a direction opposite to D.

Figure 8:
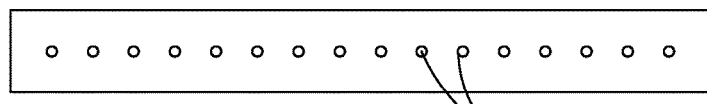

Referring to FIGS. 1 and 8, the chemical delivery system 140 is coupled to the chamber 110 by a gas injection assembly 190. The gas injection assembly includes a plurality of apertures 192 that extend through the chamber wall 112. The apertures 192 can be arranged in a row, e.g., parallel to the axis of rotation 153 of the drive shaft 152. Although FIG. 8 illustrates a single row of apertures 192, the system can have multiple rows of apertures. In particular, there can be different rows of apertures for the different reactants or precursors. In addition, there can be multiples rows of apertures for a given reactant and/or precursor.

The apertures 192 are located below the expected position of the top surface 12 of the particle bed. In particular, the apertures 192 through the chamber wall 112 can be located in the lower portion 110b of the chamber 110. For example, the apertures 192 can be extend through the curved semi-circular portion of the side wall 112. The apertures 192 can be positioned in the lower half, e.g., the lower third, e.g., lower quarter, e.g., lower fifth (as measured by vertically) of the chamber wall 112 of the lower portion 110b. The apertures can have a diameter of 0.5 to 3 mm. Although FIG. 1 illustrates the apertures 192 are illustrated as extending through the chamber wall horizontally, this is not required, as explained further below.

Figure 9:
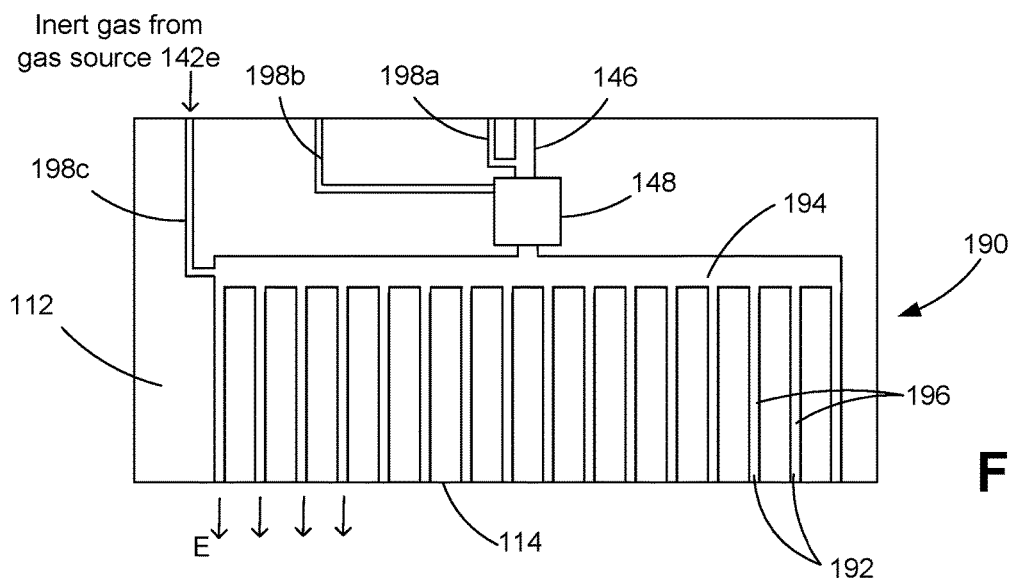

Referring to FIGS. 1 and 9, the gas injection assembly 190 includes a manifold 194 with multiple channels 196 leading from the manifold 194 to the apertures 192. The manifold 194 and channels 196 can be formed as passages through a solid body 196 that provides a portion of the chamber wall 112. The vaporizer 148 can be positioned immediately upstream of the manifold 194.

An inert carrier gas, e.g., $N_2$, can flow from one of the fluid sources, e.g., the fluid source 142e, through one or more passages 198 into the manifold 194. In operation, the carrier gas can flow continuously into the manifold 194, i.e., whether or not the precursor or reactor gas is flowing into the manifold 194. As one example, the carrier gas can be injected through a passage 198a into the fluid line 146 before the liquid reaches the vaporizer. As another example, the carrier gas can be injected through a passage 198b directly into the vaporizer 148. As another example, the carrier gas can be injected through a passage 198c directly into the manifold 194.

When the precursor or reactor gas is not being injected into the chamber 110 through the manifold 194, the flow of the carrier gas can prevent backstreaming into the aperture 192 of the another precursor or reactor gas that is being injected from another manifold. The flow of carrier gas can also prevent fouling of the aperture 192, e.g., blockage of the aperture, by the particles in the particle bed 10. In addition, the carrier gas can provide the purge gas for the purge operation when the precursor or reactor gas is not being injected into the chamber 110.

The flow of carrier gas into the vaporizer 148 when the precursor gas is also flowing can improve vaporization of the precursor or reactant liquid. Without being limited by any particular theory, the carrier gas flow can assist in shearing the liquid during aerosolization, which can lead to smaller droplet size, which can be vaporized more quickly. Flow of the carrier gas into the manifold 148 when the precursor gas is also flowing can assist in drawing precursor gas out of the vaporizer.

Gas from the chemical delivery system 140, flows out of the apertures in a direction (indicated by arrow E) into the chamber 110. Assuming that the chamber 110 is partially filled with the particles, the gas is injected near a bottom of the particle bed 10. Thus, the chemicals of the gas must "bubble" through the body of the particle bed 10 to escape and be drawn out by the vacuum port 132. This can help ensure that the particles are uniformly exposed to the gas.

The direction of rotation of the paddle assembly 150 (indicated by arrow C) can such that the paddle sweeps across the apertures 192 in a direction that has a component in the same direction (i.e., no anti-parallel component) as the gas flow (indicated by arrow E). This can prevent the particles from being forced back against the gas flow and blocking the apertures 192.

Figure 10:
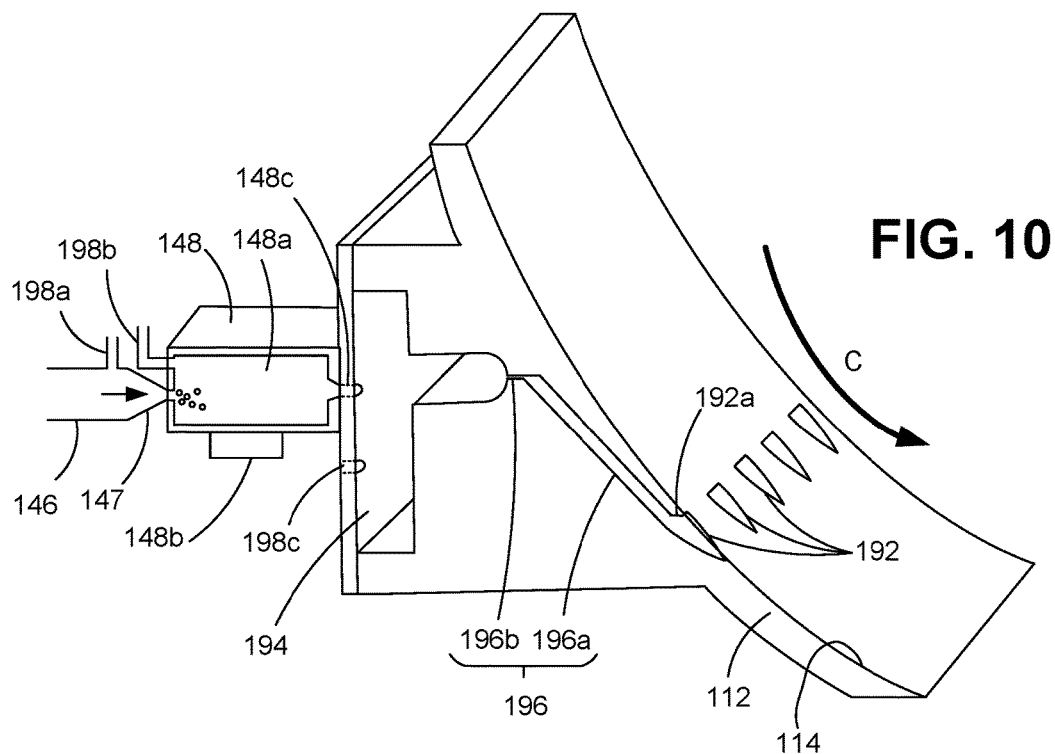

Referring to FIG. 10, the gas injection assembly 190 can be configured to inject gas into the chamber 110 with a direction of gas flow that is substantially parallel to the instantaneous direction of motion of the paddle 154 as it passes over the apertures 192. Stated differently, the direction of gas flow at injection can be substantially tangent to the curved inner surface 114 of the cylindrical bottom portion 110a of the chamber 110. In addition, the gas injection assembly 190 can be positioned and oriented such that the gas flow is toward the bottom of the chamber 110 (rather than toward the surface of the powder bed).

Each channel 196 can include a first channel portion 196a that extends at a shallow angle toward the inner surface 114. This first channel portion 196a opens to the chamber 110 at apertures 192. As shown in FIG. 10, the apertures 192 can be scalloped recesses with a sharp indent and then a depth that gradually decreases along the direction of rotation (shown by arrow C) of the paddles 154. The first channel portion 196a can open to a ceiling 192a of the aperture 192 formed by the sharp indent. This configuration can reduce likelihood of particles from entering the channel 196. In addition, the first channel portion 196a can wider than the expected diameter of the particles. This can reduce the risk of particles clogging the first channel portion 196a.

The channel 196 also includes a second channel portion 196b that extends between the manifold 194 and the first channel portion 196a. The second channel portion 196b is narrower than the first channel portion 196a. This narrower channel portion 196b controls flow rate and flow distribution out of the manifold 194.

The vaporizer 148 can include an internal cavity 148a surrounded by walls that are heated by a heater 148b, e.g., a resistive heater, thermoelectric heater, heat lamp, etc. The fluid supply passage 146 is coupled to the cavity 148a by a nozzle 147. As the liquid passes through the nozzle 147, it is aerosolized. The combination of elevated temperature, rapid pressure change and high surface area of aerosol enables rapid vaporization of large quantities of the reactant or precursor. The cavity 149a of the vaporizer 148 can extend along a substantial portion, e.g., at least half, of the length of the chamber 110. The liquid reactant or precursor can be injected through the nozzle 147 at one of the cavity, and an aperture 148c for the reactant or precursor vapor to pass into the manifold 194 can be located at opposite end of the cavity chamber (along the length of the chamber 110).

As noted above, the vaporizer 148 can be integrated into the body that provides the manifold. For example, the vaporizer 148, manifold 194 and channels 196 can all be part of a single unitary body.

In some implementations, one or more temperature control components are integrated into the chamber walls 112 to permit control of the temperature of the chamber 110. For example, resistive heater, a thermoelectric cooler, a heat exchanger, or coolant flowing in cooling channels in the chamber wall, or other component in or on the side walls 112.

The reactor system 10 also includes a controller 105 coupled to the various controllable components, e.g., the vacuum source 130, the chemical delivery system 140, the motor 160, the temperature control system, etc., to control operation of the reactor system 100. The controller 105 can also be coupled to various sensors, e.g., pressure sensors, flow meters, etc., to provide closed loop control of the pressure of the gasses in the chamber 110.

In general, the controller 105 is configured to operate the reactor system 100 in accord with a "recipe." The recipe specifies an operating value for each controllable element as a function of time. For example, the recipe can specify the times during which the vacuum source 130 is to operate, the times of and flow rate for each gas source 142a-142e, the rotation rate of the drive shaft 152 as set by the motor 160, etc. The controller 105 can receive the recipe as computer-readable data (e.g., that is stored on a non-transitory computer readable medium).

The controller 105 and other computing devices part of systems described herein can be implemented in digital electronic circuitry, or in computer software, firmware, or hardware. For example, the controller can include a processor to execute a computer program as stored in a computer program product, e.g., in a non-transitory machine readable storage medium. Such a computer program (also known as a program, software, software application, or code) can be written in any form of programming language, including compiled or interpreted languages, and it can be deployed in any form, including as a standalone program or as a module, component, subroutine, or other unit suitable for use in a computing environment. In some implementations, the controller 105 is a general purpose programmable computer. In some implementations, the controller can be implemented using special purpose logic circuitry, e.g., an FPGA (field programmable gate array) or an ASIC (application specific integrated circuit).

For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Operation

Initially, particles are loaded into the chamber 110 in the reactor system 100. The particles can have a solid core comprising a drug, e.g., one of the drugs discussed above. The solid core can optionally also include an excipient. Once any access ports are sealed, the controller 105 operates the reactor system 100 according to the recipe in order to form the thin-film oxide layers and/or thin polymer layers on the particles.

In operation, the reactor system 100 performs an ALD and/or an MLD thin-film coating process by introducing gaseous precursors of the coating into the chamber 110. The gaseous precursors are spiked alternatively into the reactor chamber 110. This permits the deposition process to be a solvent-free process. The half-reactions of the deposition process are self-limiting, which can provide Angstrom or nanometer level control of deposition. In addition, the ALD and/or MLD reaction can be performed at low temperature conditions, such as below 50° C., e.g., below 35° C.

Suitable reactants for ALD methods include any of or a combination of the following: monomer vapor, metal-organics, metal halides, oxidants, such as ozone or water vapor, and polymer or nanoparticle aerosol (dry or wet). For example, the first fluid source 142a can provide gaseous trimethylaluminum (TMA) or titanium tetrachloride (TiCl4), whereas the second gas source 142b can provide water. For MLD methods, as an example, the fluid source 142c can provide adipoyl chloride, and the fourth fluid 142d can provide vaporous or gaseous ethylene diamine.

In operation, one of the gasses flows from the chemical delivery system 140 into the particle bed 10 in the lower portion 110a of the chamber 110 as the paddle assembly 150 rotates. Rotation of the paddle assembly 150 agitates the particles to keep them separate, ensuring a large surface area of the particles remains exposed. This permits fast, uniform interaction of the particle surface with the process gas.

For both an ALD process and an MLD process, two reactant gases are alternately supplied to the chamber 110, with each step of supplying a reactant gas followed by a purge cycle in which the inert gas is supplied to the chamber 110 to force out the reactant gas and byproducts used in the prior step.

As noted above, the coating process can be performed at low processing temperature, e.g., below 50° C., e.g., at or below 35° C. In particular, the particles can remain or be maintained at such temperatures during all of steps (i)-(ix) noted above. In general, the temperature of the interior of the reactor chamber does not exceed 35° C. during of steps (i)-(ix). This can be achieved by having the first reactant gas, second reactant gas and inert gas be injected into the chamber at such temperatures during the respective cycles. In addition, physical components of the chamber can remain or be maintained at such temperatures, e.g., using a cooling system, e.g., a thermoelectric cooler, if necessary.

In some implementations, the controller can cause the reactor system 100 to first deposit an oxide layer on the drug-containing particles, and then deposit a polymer layer over the oxide layer on the particles, e.g., using the process described above. In some implementations, the controller can cause the reactor system 100 alternate between depositing an oxide layer and depositing a polymer layer on the drug-containing particles, so as to form a multi-layer structure with layers of alternating composition.

Continuous Flow Operation

For an ALD process, the controller 105 can operate the reactor system 100 as follows.

In a first reactant half-cycle, while the motor 160 rotates the paddle wheel 150 to agitate the particles:

i) The gas distribution system 140 is operated to flow the first reactant gas, e.g., TMA, from the source 142a into the chamber 110 until the particle bed 10 is saturated with the first reactant gas. For example, the first reactant gas can flow at a specified flow rate and for a specified period of time, or until a sensor measures a specified first pressure or partial pressure of the first reactant gas in the upper portion 110b of the chamber. In some implementations, the first reactant gas is mixed with an inert gas as it flows into the chamber. The specified pressure or partial pressure can be 0.1 Torr to half of the saturation pressure of the reactant gas.

ii) Flow of the first reactant gas is halted, and the vacuum source 140 evacuates the chamber 110, e.g., down to pressures below 1 Torr, e.g., to 1 to 100 mTorr, e.g., 50 mTorr.

These steps (i)-(ii) can be repeated a number of times set by the recipe, e.g., two to ten times.

Next, in a first purge cycle, while the motor 160 rotates the paddle wheel 150 to agitate the particles:

iii) The gas distribution system 140 is operated to flow only inert gas, e.g., $N_2$, from the source 142e into the chamber 110. The inert gas can flow at a specified flow rate and for a specified period of time, or until a sensor measures a specified second pressure of the inert gas in the upper portion 110b of the chamber. The second specified pressure can be 1 to 100 Torr.

iv) The vacuum pump 140 evacuates the chamber 110, e.g., down to pressures below 1 Torr, e.g., to 1 to 500 mTorr, e.g., 50 mTorr.

These steps (iii)-(iv) can be repeated a number of times set by the recipe, e.g., six to twenty times.

In a second reactant half-cycle, while the motor 160 rotates the paddle assembly 150 to agitate the particles:

v) The gas distribution system 30 is operated to flow the second reactant gas, e.g., $H_2O$, from the source 142b into the chamber 110 until the particle bed 10 is saturated with the second reactant gas. Again, the second reactant gas can flow at a specified flow rate and for a specified period of time, or until a sensor measures a specified third pressure or partial pressure of the second reactant gas in the upper portion 110b of the chamber. In some implementations, the second reactant gas is mixed with an inert gas as it flows into the chamber. The third pressure can be 0.1 Torr to half of the saturation pressure of the second reactant gas.

vi) The vacuum pump 140 evacuates the chamber 110, e.g., down to pressures below 1 Torr, e.g., to 1 to 500 mTorr, e.g., 50 mTorr.

These steps (v)-(vi) can be repeated a number of times set by the recipe, e.g., two to ten times.

Next, a second purge cycle is performed. This second purge cycle with steps (vii) and (vii) can be identical to the first purge cycle, or can have a different number of repetitions of the steps (iii)-(iv) and/or different specified pressure.

The cycle of the first reactant half-cycle, first purge cycle, second reactant half cycle and second purge cycle can be repeated a number of times set by the recipe, e.g., one to ten times.

The operation is discussed above with an ALD process, but the operation is similar for MLD. In particular, in steps (i) and (v), the reactant gasses are substituted with appropriate process gasses and pressures for deposition of a polymer layer. For example, step (i) can use vaporous or gaseous adipoyl chloride, and step (v) can use vaporous ethylene diamine.

Moreover, although operation is discussed above with an ALD or MLD process, the system could be used for a chemical vapor deposition (CVD) process. In this case, both reactants are flowed simultaneously into the chamber 110 so as to react inside the chamber, e.g., during step (i). The second reactant half-cycle can be omitted.

Pulsed Flow Operation

In another implementation, one or more of the gases (e.g., the reactant gases and/or the inert gas) can be supplied in pulses in which the chamber 110 is filled with the gas to a specified pressure, a delay time is permitted to pass, and the chamber is evacuated by the vacuum source 140 before the next pulse commences.

In particular, for an ALD process, the controller 105 can operate the reactor system 100 as follows.

In a first reactant half-cycle, while the motor 160 rotates the paddle wheel 150 to agitate the particles:

i) The gas distribution system 140 is operated to flow the first reactant gas, e.g., TMA, from the source 142a into the chamber 110 until a first specified pressure is achieved in the upper portion 110b of the chamber. The specified pressure can be 0.1 Torr to half of the saturation pressure of the reactant gas.

ii) Flow of the first reactant gas is halted, and a specified delay time is permitted to pass, e.g., as measured by a timer in the controller. This permits the first reactant to flow through the particle bed 10 in the chamber 110 and react with the surface of the particles.

iii) The vacuum pump 140 evacuates the chamber 110, e.g., down to pressures below 1 Torr, e.g., to 1 to 100 mTorr, e.g., 50 mTorr.

These steps (i)-(iii) can be repeated a number of times set by the recipe, e.g., two to ten times.

Next, in a first purge cycle, while the motor 160 rotates the paddle wheel 150 to agitate the particles:

iv) The gas distribution system 140 is operated to flow the inert gas, e.g., $N_2$, from the source 142e into the chamber 110 until a second specified pressure is achieved. The second specified pressure can be 1 to 100 Torr.

v) Flow of the inert gas is halted, and a specified delay time is permitted to pass, e.g., as measured by the timer in the controller. This permits the inert gas to diffuse through the particles in the particle bed 10 to displace the reactant gas and any vaporous by-products.

vi) The vacuum pump 140 evacuates the chamber 110, e.g., down to pressures below 1 Torr, e.g., to 1 to 500 mTorr, e.g., 50 mTorr.

These steps (iv)-(vi) can be repeated a number of times set by the recipe, e.g., six to twenty times.

In a second reactant half-cycle, while the motor 160 rotates the paddle assembly 150 to agitate the particles:

vii) The gas distribution system 30 is operated to flow the second reactant gas, e.g., $H_2O$, from the source 142b into the chamber 110 until a third specified pressure is achieved. The third pressure can be 0.1 Torr to half of the saturation pressure of the reactant gas.

viii) Flow of the second reactant gas is halted, and a specified delay time is permitted to pass, e.g., as measured by the timer in the controller. This permits the second reactant gas to flow through the particle bed 10 and react with the surface of the particles inside the drum chamber 110.

ix) The vacuum pump 140 evacuates the chamber 110, e.g., down to pressures below 1 Torr, e.g., to 1 to 500 mTorr, e.g., 50 mTorr.

These steps (vii)-(ix) can be repeated a number of times set by the recipe, e.g., two to ten times.

Next, a second purge cycle is performed. This second purge cycle can be identical to the first purge cycle, or can have a different number of repetitions of the steps (iv)-(vi) and/or different delay time and/or different pressure.

The cycle of the first reactant half-cycle, first purge cycle, second reactant half cycle and second purge cycle can be repeated a number of times set by the recipe, e.g., one to ten times.

Moreover, one or more of the gases (e.g., the reactant gases and/or the inert gas) can be supplied in pulses in which the chamber 110 is filled with the gas to a specified pressure, a delay time is permitted to pass, and the chamber is evacuated by the vacuum source 140 before the next pulse commences.

The operation is discussed above with an ALD process, but the operation is similar for MLD. In particular, in steps (i) and (vii), the reactant gasses are substituted with appropriate process gasses and pressures for deposition of a polymer layer. For example, step (i) can use vaporous or gaseous adipoyl chloride, and step (vii) can use are vaporous ethylene diamine.

Moreover, although operation is discussed above with an ALD or MLD process, the system could be used for a chemical vapor deposition (CVD) process. In this case, both reactants are flowed simultaneously into the chamber 110 so as to react inside the chamber, e.g., during step (i). The second reactant half-cycle can be omitted.

Use of Gas Flow for De-Agglomeration

As discussed above, even with the agitation of the particles by paddles, the particles can still form micro-agglomerates, e.g., clumps of several particles or groups forming agglomerates of up to 10× the primary particle size.

However, one or more of the gases (e.g., the reactant gases and/or the inert gas) can be injected in a manner to cause de-agglomeration of the particles in the particle bed in the chamber 110. Such an approach enables this de-agglomeration to occur in-situ, e.g., during the purge step between reactant gas exposures, thus improving process throughput and improving yield by eliminating the vacuum break and atmospheric exposure that can occur with the ex-situ process of de-agglomeration.

A related issue is overall management of gas-particle interaction. During delivery of a reactant gas to the chamber for deposition, it is desirable for the reactant gas to be moving slowly to provide the process gas with as long a residence time within the powder as possible, while still sufficiently quickly to prevent particles from backstreaming into the manifold. If the velocity of the reactant gas is too high, the reactant gas will not have time or exposure to react, and can create rat holes.

De agglomeration can be performed by the reactant gas, the purge gas, or both. Assuming that the purge gas, i.e., the inert gas, is to be used for de-agglomeration, the gas needs to be fast enough to perform de-agglomeration, but not so fast that "rat holes" are formed through the powder bed. The paddle rotation rate can be combined with higher velocity purge gas to reduce ratholing with jet de-aggregation. In addition, the gas flow needs to be sufficiently slow that powder stays in the powder bed rather than being "blown" out of the powder bed and into the exhaust system. Assuming that the reactant gas is to be used for de-agglomeration, it would be subject to the constraints for the inert gas and the additional constraints noted above for deposition.

The specific flow and pressure regimes will depend on particle size and composition, degree of agitation by the paddles.

During processing steps with the reactive gas, the chamber can be maintained at pressure of 1-100 Torr, e.g., to 20-50 Torr, and the flow velocity of the reactive gas (or mixture of reactive gas and inert gas) can be under 10 m/s, e.g., 1-10 m/s. In some implementations these speeds, e.g., less than 10 m/s, can be sufficient to provide de-agglomeration by the reactive gas (or mixture of reactive gas and inert gas) during the deposition step.

In some implementations, during purging steps with the inert gas, the purge gas flows into the processing chamber at the same velocity, e.g., 1-10 m/s, as the gas flow in the deposition step. In some implementations, the purge gas flows into the processing chamber at a higher velocity than in the deposition step, but still less than 10 m/s. In some implementations, the flow velocity can be increased to 30-200 m/s, e.g., 50-100 m/s. Such a velocity is sufficient to break micro-aggregates, but not enough to break the primary particles. Velocities can be kept below the supersonic velocity range of a jet mill, e.g., less than 340 m/s. In some implementations, the velocity of the purge gas is increased for a portion of the purge step, e.g., to above 30 m/s, but is kept at a lower velocity, e.g., less than 10 m/s or the same velocity as in the deposition step, for a remainder of the purge step.

The chamber pressure can be set during the purge step to a pressure below that maintained for the deposition step, e.g., less than 20 Torr, e.g., 1-20 Torr.

In some implementations, the de-agglomeration is temporary, e.g., the particles can re-agglomerate before a subsequent deposition. However, over the course of multiple deposition cycles, by breaking up micro-agglomerates so that new contact points are formed during re-agglomeration, the entirety of the particles should still be coated. In some implementations, the de-agglomeration lasts sufficiently long for a concurrent or subsequent deposition step to effectively coat an entirety of the particles, but the particles re-agglomerate by the time the particles are removed from the chamber.

CONCLUSION

The present disclosure provides apparatus for and methods of preparing pharmaceutical compositions comprising API containing particles encapsulated by one or more layers of oxide and/or one or more layers of a polymer. The coating layers are conformal and of controlled thickness from several nanometers to several micrometers in total. The articles to be coated can be composed of only API or a combination of API and one or more excipients. The coating process described herein can provide an API with an increased glass transition temperature for the API relative to uncoated API, a decreased rate of crystallization for an amorphous form of the API relative to uncoated API, and decreased surface mobility of API molecules in the particle compared to uncoated API. Importantly, particle dissolution can be altered. Because the coating is relatively thin, drug products with high drug loading can be achieved. Finally, there are benefits with respect to cost and ease of manufacture because multiple coatings can be applied in the same reactor.

Terms of relative positioning are used to refer to relative positioning of components within the system or orientation of components during operation; it should be understood that the reactor system could be held in a vertical orientation or some other orientation during shipping, assembly, etc.

A number of embodiments of the invention have been described. Nevertheless, it will be understood that various modifications may be made without departing from the spirit and scope of the invention.

What is claimed is:

1. A reactor for coating particles, comprising:
a stationary vacuum chamber to hold a bed of particles to be coated, the vacuum chamber having a lower portion that forms a half-cylinder and an upper portion;
a vacuum port in the upper portion of the vacuum chamber;
a motor;
a paddle assembly including:
a rotatable drive shaft extending through the vacuum chamber along an axial axis of the half-cylinder,
a plurality of paddles extending radially from the drive shaft such that rotation of the drive shaft by the motor orbits the plurality of paddles about the drive shaft; and
a first gas injection assembly configured to receive a first fluid from one or more fluid sources and comprising apertures extending through a wall of the lower portion of the stationary vacuum chamber and to an inner surface of the half-cylinder formed by the lower portion of the stationary vacuum chamber and configured to inject a first reactant or precursor gas into the lower portion of the vacuum chamber such that the first reactant or precursor gas flow injected into the vacuum chamber is substantially tangent to a curvature of the inner surface of the half-cylinder formed by the lower portion, wherein the apertures comprise a first plurality of apertures extending in a first row parallel to the axial axis, and wherein the first gas injection assembly is configured to inject the first reactant or precursor gas through the first plurality of apertures.

2. The reactor of claim 1, wherein the first gas injection assembly is configured to inject the first reactant or precursor gas in a direction perpendicular to the axial axis.

3. The reactor of claim 1, wherein the first plurality of apertures are positioned in a lower half of the lower portion of the vacuum chamber.

4. The reactor of claim 3, wherein the first plurality of apertures are positioned in a lower quarter of the lower portion of the vacuum chamber.

5. The reactor of claim 1, further comprising a second gas injection assembly configured to receive a second fluid from the one or more fluid sources and having apertures extending through the wall of the lower portion of the stationary vacuum chamber and to an inner surface of the half-cylinder formed by the lower portion of the stationary vacuum chamber and configured to inject a second reactant or precursor gas into the lower portion of the vacuum chamber such that the second reactant or precursor gas flow injected into the vacuum chamber is substantially tangent to a curvature of the inner surface of the half-cylinder formed by the lower portion.

6. The reactor of claim 5, wherein the second gas injection assembly comprises second plurality of apertures extending in a second row parallel to the axial axis, and wherein the second gas injection assembly is configured to inject the second reactant or precursor gas through the second plurality of apertures.

7. The reactor of claim 1, wherein the first gas injection assembly include a manifold and a plurality of channels extending from the manifold to the first plurality of apertures.

8. The reactor of claim 7, wherein each channel opens in a ceiling of a corresponding aperture.

9. The reactor of claim 7, comprising a restriction between the manifold and the plurality of channels.

10. The reactor of claim 1, further comprising a controller configured to keep a flow rate of the reactant or precursor gas flow sufficiently slow that powder stays in the bed of particles.

11. A reactor for coating particles, comprising:
- a stationary vacuum chamber to hold a bed of particles to be coated, the vacuum chamber having a lower portion that forms a half-cylinder and an upper portion;
- a vacuum port in the upper portion of the vacuum chamber;
- a motor;
- a paddle assembly including:
  - a rotatable drive shaft extending through the vacuum chamber along an axial axis of the half-cylinder,
  - a plurality of paddles extending radially from the drive shaft such that rotation of the drive shaft by the motor orbits the plurality of paddles about the drive shaft; and
- a first gas injection assembly configured to receive a first liquid from one or more fluid sources, the first gas injection assembly including a vaporizer to convert the first liquid to a first reactant or precursor gas, a manifold to receive the first reactant or precursor gas from the vaporizer, and a plurality of channels leading from the manifold to a plurality of apertures,
  - wherein the plurality of apertures extend through a wall of the lower portion of the stationary vacuum chamber to an inner surface of the half-cylinder formed by the lower portion of the stationary vacuum chamber, and
  - wherein the plurality of apertures are configured to inject the first reactant or precursor gas such that the first reactant or precursor gas flow injected into the vacuum chamber is substantially tangent to a curvature of the inner surface of the half-cylinder formed by the lower portion of the vacuum chamber.

12. The reactor of claim 11, wherein the vaporizer is immediately adjacent the manifold.

13. The reactor of claim 12, wherein the vaporizer, manifold and plurality of channels are formed in a unitary body.

14. The reactor of claim 13, wherein the vaporizer comprises a cavity, a heater to heat walls of the cavity, and a nozzle to aerosolize the first liquid as the first liquid passes into cavity.

15. The reactor of claim 14, wherein the plurality of channels are fluidically connected directly to the cavity.

16. The reactor of claim 11, comprising a passage connecting the one or more fluid sources to deliver an inert gas to the manifold.

17. The reactor of claim 16, wherein the passage is fluidically connected directly to the manifold.

18. The reactor of claim 16, wherein the passage is fluidically connected directly to an inlet that carries the first liquid.

* * * * *